(12) United States Patent
Inakagata et al.

(10) Patent No.: US 7,478,911 B2
(45) Date of Patent: Jan. 20, 2009

(54) PERIMETER

(75) Inventors: Satoru Inakagata, Nara (JP); Shuji Murakami, Takaishi (JP); Shogo Fukushima, Moriguchi (JP); Hideo Fukunaga, Yokkaichi (JP); Akio Tabuchi, Okayama (JP); Kazutaka Kani, Kobe (JP); Fumiatsu Maeda, Kurashiki (JP)

(73) Assignee: Matsushita Electric Works, Ltd., Kadoma-shi (JP)

( * ) Notice: Subject to any disclaimer, the term of this patent is extended or adjusted under 35 U.S.C. 154(b) by 126 days.

(21) Appl. No.: 11/662,640

(22) PCT Filed: Sep. 5, 2005

(86) PCT No.: PCT/JP2005/016232

§ 371 (c)(1),
(2), (4) Date: Mar. 13, 2007

(87) PCT Pub. No.: WO2006/030658

PCT Pub. Date: Mar. 23, 2006

(65) Prior Publication Data

US 2008/0117384 A1    May 22, 2008

(30) Foreign Application Priority Data

Sep. 15, 2004  (JP)  ............................. 2004-268638
Mar. 23, 2005  (JP)  ............................. 2005-084550

(51) Int. Cl.
*A61B 3/02*  (2006.01)

(52) U.S. Cl. ....................................... 351/224; 351/243
(58) Field of Classification Search .......... 351/205–246
See application file for complete search history.

(56) References Cited

U.S. PATENT DOCUMENTS 7,244,027 B2 *  7/2007  Sumiya ...................... 351/224
7,309,129 B2 * 12/2007  Suzuki ...................... 351/224

FOREIGN PATENT DOCUMENTS

| JP | 5-146404    | 6/1993 |
| JP | 2003-164425 | 6/2003 |
| JP | 2004-121707 | 4/2004 |
| JP | 2004-216118 | 8/2004 |

OTHER PUBLICATIONS

Takeshi Yoshitomi et al., "Objective Perimetry—Pupil Perimetry" Folia Ophthalmologica Japonica, vol. 49, Nov. 9, 1998, pp. 733-737. / English Abstract is attached. / Discussed in the specification.

* cited by examiner

*Primary Examiner*—Mohammed Hasan
(74) *Attorney, Agent, or Firm*—Edwards Angell Palmer & Dodge LLP

(57) ABSTRACT

The perimeter comprises a display device 1, infrared light-emitting diodes 2, a CCD camera 3, a half mirror 4, an image processing device 5, a computer 6, and an operating switch 7. The computer 6 shows a fixed eye-target for fixing a line of sight of a subject and a light stimulus eye-target for giving a light stimulus to a pupil of the subject at a plurality of predetermined positions on the display device 1. The infrared light-emitting diodes 2 irradiate infrared light to an eye of the subject. The CCD camera 3 takes an image of the eye of the subject using the infrared light irradiated from the infrared light-emitting diodes 2. The image processing device 5 detects a pupil diameter of the subject based on the image taken by the CCD camera 3. The computer 6 measures a visual field of the subject based on the change of the pupil diameter of the subject detected by the image processing device 5. The feature of the present invention resides in that the display device 1 comprises a display device capable of adjusting background luminance of a screen and brightness of the light stimulus eye-target separately.

17 Claims, 10 Drawing Sheets

PERIMETER

TECHNICAL FIELD

The present invention relates to a perimeter for measuring a visual field of a subject.

BACKGROUND ART

Examination of visual field (namely, a perimetry) is performed to diagnose a constriction of visual field which is a symptom of glaucoma and so on. In the conventional perimetry, the visual field of the subject is measured by showing an eye-target at a specific point in front of an eye of a subject and having the subject answer a question whether he or she can see the eye-target. Such an examination is a subjective examination based on a subjective answer of the subject, and a visual field range of the subject is identified by measuring the visual field multiple times while changing the showing position of the eye-target one after another. In such a subjective examination, there was a problem that an inspection result is easily swayed by a physical condition and concentration and so on of the subject and an accurate examination can not be done. Furthermore, because a series of operations of showing the eye-target and then having the subject answer have to be repeated many times, there are also problems that it takes a long time to do the inspection and a burden on the subject is large.

Folia opthalmologica Japonica (p. 733-737, Volume 49, Number 9, 1998) discloses a perimeter capable of performing an objective perimetry which does not depend on the subjective answer of the subject. In this perimeter, in order to measure the visual field of the subject, a fixed eye-target is projected on a screen provided in front of the eyes of the subject, and a light stimulus eye-target is projected at a plurality of positions on the screen one after another in a condition where the subject is gazing at the fixed eye-target so as to give a light stimulus to a retina of the subject, and a miotic response of the pupil by the light stimulation (namely, a pupillary light reflex) is detected.

Furthermore, Japanese Non-examined Patent Publication No. 5-146404 and Japanese Non-examined Patent Publication No. 2004-216118 disclose a perimeter which objectively measures the visual field of the subject by showing a fixed eye-target and a light stimulus eye-target using a light emitting device such as a light-emitting diode and detecting the presence or absence of the pupillary light reflex at the time when the light stimulation is given to the subject.

In such an objective perimeter, the darker the background luminance to the light stimulus eye-target is, the easier the detection of the pupillary light reflex becomes. But, when the background luminance is too dark, the light of the light stimulus eye-target is scattered, and therefore the light stimulus is not given to an accurate position of the retina of the subject. Furthermore, it takes a long time for the pupil of the subject to adapt to the darkness of the background, whereby the inspection time becomes long. On the other hand, when the background luminance is too bright, the brightness difference between the background and the light stimulus eye-target becomes small, and the pupillary light reflex also becomes small, and therefore, the detection of the reaction becomes difficult. Furthermore, it is preferable that the size of the light stimulus eye-target and stimulus intensity thereof are changed according to the subject.

As mentioned above, in the objective perimeter, it is preferable that the background luminance, the brightness of the eye-target, and the size of the eye-target and so on are adjustable freely. But, in the above mentioned conventional perimeter, because the eye-target is projected on a screen or the light stimulus eye-target is shown by using a light-emitting diode, there was a problem that it is not possible to easily adjust the background luminance, the brightness of the eye-target, and the size of the eye-target.

DISCLOSURE OF THE INVENTION

In view of the above problem, the object of the present invention is to provide an objective perimeter capable of adjusting the background luminance, the brightness of the eye-target, and the size of the eye-target and so on easily and capable of measuring the visual field accurately in a short time.

A perimeter of the present invention comprises a display means, an eye-target control means, an infrared light irradiating means, an imaging means, a case, a pupil-detection means, and a visual field measuring means. The eye-target control means shows a fixed eye-target for fixing a line of sight of a subject and a light stimulus eye-target for giving a light stimulus to a pupil of the subject at a plurality of predetermined positions on said display means. The infrared light irradiating means irradiates infrared light to an eye of the subject. The imaging means takes an image of the eye of the subject using the infrared light irradiated from the infrared light irradiating means. The case houses the display means, the infrared light irradiating means, and the imaging means therein, and the case has a peephole through which the subject looks at the fixed eye-target and the light stimulus eye-target displayed on the display means from outside. The pupil detection means detects a pupil diameter of the subject based on the image taken by the imaging means. The visual field measuring means measures a visual field of the subject based on a change of the pupil diameter of the subject detected by the pupil detection means when the eye-target control means shows the light stimulus eye-target in a condition where the subject looks at the fixed eye-target.

The feature of the present invention resides in that the display means comprises a display device capable of adjusting background luminance of a screen and brightness of the light stimulus eye-target separately. Therefore, the perimeter of the present invention can easily adjust the background luminance of the screen and the brightness of the light stimulus eye-target, and can set the background luminance of the screen and the brightness of the light stimulus eye-target to optimal values. Of course, because it is also possible to change the size of the eye-target and a display time (showing time) of the eye-target easily, the perimeter of the present invention can display an optimal eye-target according to a subject. Therefore, the perimeter of the present invention can measure the visual field accurately in a short time.

Preferably, the perimeter further comprises a display position adjusting means capable of adjusting a position of the display means in a vertical direction and/or a horizontal direction and/or a back-and-forth direction with respect to said peephole. By providing the display position adjusting means, it becomes possible to move the display means to an optimal position according to the position of the eye of the subject and vision of the subject.

Preferably, the perimeter further comprises an imaging device adjusting means capable of adjusting an imaging position and imaging direction of the imaging means. By providing the imaging device adjusting means, it becomes possible to adjust the position and the angle of the imaging means according to the pupil of the subject. In this case, it is more preferable that the perimeter further comprises an imaging device control means for adjusting the imaging position and the imaging direction of said imaging means through the imaging device adjusting means based on a detection result of the pupil detection means so that the pupil diameter of the subject peaks. By providing the imaging device control means, it becomes possible to automatically adjust the imaging means to an optimal position and to an optimal direction.

Preferably, the perimeter further comprises an operating switch which outputs an operation signal to the visual field measuring means in response to an operation of the subject, and the visual field measuring means measures the visual field based on the change of the pupil diameter of the subject and an input of the operation signal from the operating switch. In this case, it is possible to perform a subjective perimetry in addition to the objective perimetry, so that reliability of the measuring result can be increased.

Preferably, emissivity of an inner surface of the case is generally one (that is, the reflectance thereof is zero). In this case, the light emitted from the display means in the case is almost absorbed by the inner surface of the case, so that it is possible to prevent the light stimulus from being given to unnecessary positions of the pupil, and it is possible to increase measurement accuracy.

As to the light stimulus eye-target, a stimulus which glints instantaneously in a pulse form is generally used. Preferably, the eye-target control means shows a pulse-like light stimulus eye-target at least twice in a row on said display means. By showing the pulse-like light stimulus at least twice in a row, it becomes possible to enlarge the change of the pupil diameter even when the amount of light is the same, compared with a case where a pulse-like light stimulus is shown once, and as a result, it becomes easy to measure the visual field.

By the way, the size of the pupil diameter may wander even in a state where there is no light stimulus, and there is a case where it is difficult to judge whether the change of the pupil diameter was caused by the light stimulus or not. In such a case, it is preferable that the eye-target control means shows, on said display means, the light stimulus eye-target which changes periodically in intensity of light. By showing the light stimulus eye-target which changes periodically in intensity of light, when the change of the pupil diameter is caused by the light stimulus eye-target, the pupil diameter varies periodically in synchronization with the period of the light. Therefore, it is possible to judge easily whether the change of the pupil diameter was caused by the light stimulus or not, and reliability of the measuring result can be increased.

The light stimulus eye-target which changes periodically in intensity of light may be an optical pulse train or an eye-target whose intensity of light changes in a sine wave manner.

In this case, it is preferable that the eye-target control means has a function of changing the period of the intensity of light of the light stimulus eye-target or a function of changing a size of the light stimulus eye-target. By providing such functions, it becomes possible to show an optimal eye-target according to a subject.

Furthermore, in a case where the light stimulus eye-target which changes periodically in intensity of light is shown, it is preferable that the visual field measuring means has a function of calculating a magnitude of change of the pupil diameter from an oscillation range of the pupil diameter or amplitude of the pupil diameter. When the pupil diameter changes periodically together with the intensity of light, it is possible to easily obtain a local minimal value and a local maximal value of the pupil diameter. Therefore, by defining a difference between the local minimal value and the local maximal value of the pupil diameter, namely, an oscillation range of the pupil diameter (or amplitude of the pupil diameter which is half of the oscillation range), as the magnitude of the change of the pupil diameter, it is possible to easily obtain the magnitude of change of the pupil diameter. If a plurality of the oscillation ranges can be obtained, an average value thereof may be defined as the magnitude of the change of the pupil diameter. In this case, it is possible to moderate fluctuations (unevenness) of data.

It is also preferable that the visual field measuring means calculates a ratio between the magnitude of the change of the pupil diameter, which was obtained as above, and the intensity of light of the light stimulus eye-target, and it measures sensitivity of the visual field of the subject based on the ratio. That is, when the change of the pupil diameter is small with respect to intense light, it can be judged that the sensitivity of the visual field has deteriorated, and in that manner, the sensitivity of the visual field is measured based on the ratio.

It is also preferable that the visual field measuring means has a function of calculating synchronism between a period of the intensity of light of the light stimulus eye-target and a period of the change of the pupil diameter of the subject. In this case, it is possible to use the synchronism as one of information for judging the reliability of the measuring result.

It is also preferable that the visual field measuring means has a function of judging whether a position where the light stimulus eye-target was shown is a normal visual field area of the subject or not, based on the change of the pupil diameter of the subject. In this case, it is possible to automatically judge whether the position where the light stimulus eye-target was shown is a normal visual field area of the subject.

Preferably, the eye-target control means has a function of changing a color of the light stimulus eye-target. In this case, it is possible to perform an inspection of a pyramidal cell, which responds to color, out of retina cells.

BEST MODE FOR CARRYING OUT THE INVENTION

Figure 1:
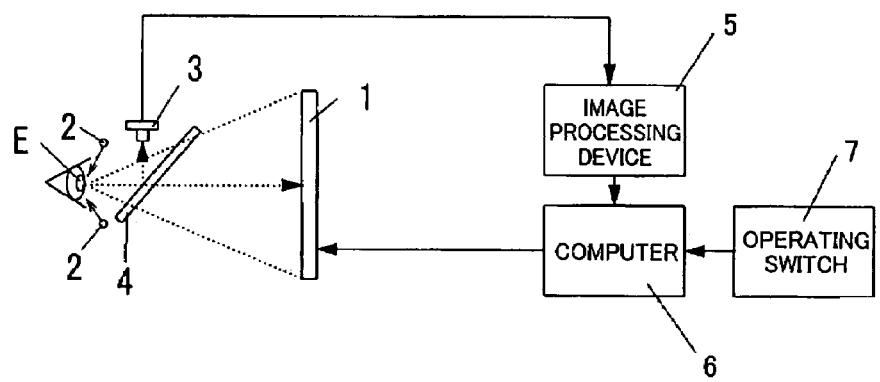
FIG. 1 is a view showing a constitution of a perimeter in accordance with an embodiment of the present invention.
Figure 2:
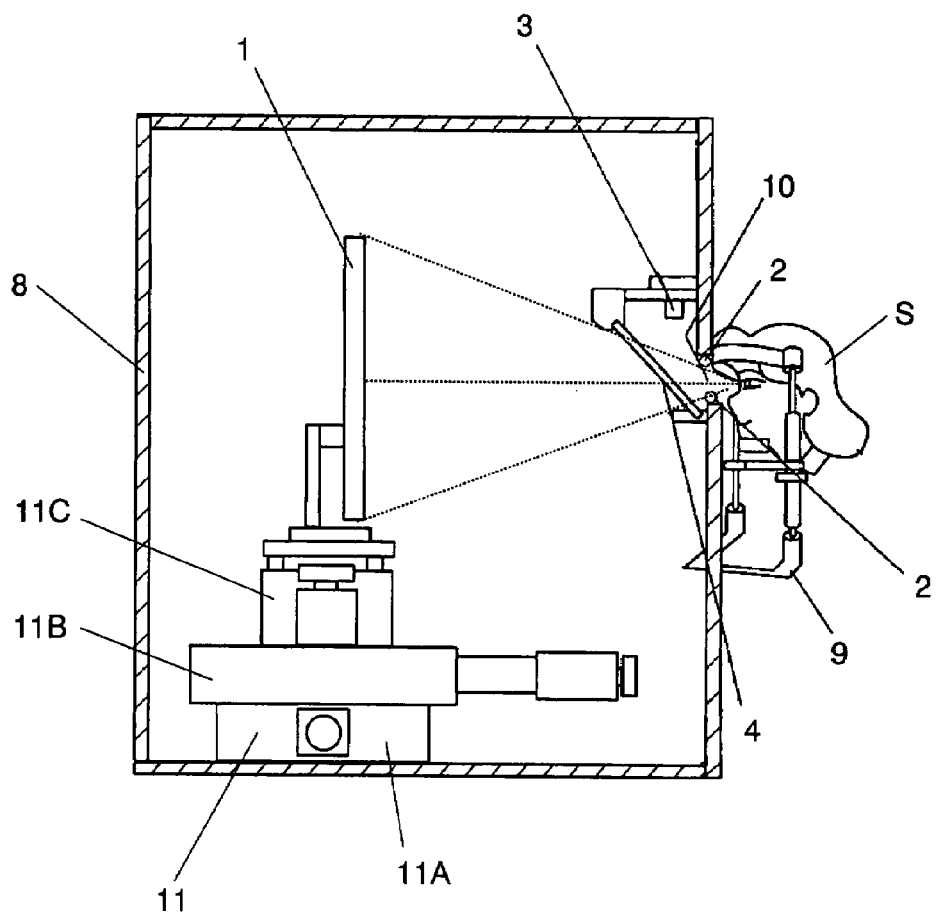
FIG. 2 is a view for explaining an internal alignment of the perimeter of FIG. 1.

Hereinafter, the present invention will be described in more detail with reference to the accompanying drawings. FIG. 1 is a view showing a constitution of a perimeter of this embodiment. The perimeter comprises a liquid-crystal display 1, infrared light-emitting diodes 2, a CCD camera 3, a half mirror 4, an image processing device 5, a computer 6, and an operating switch 7. As shown in FIG. 2, the liquid-crystal display 1, the infrared light-emitting diode 2, the CCD camera 3, and the half mirror 4 are housed in a box-shaped case 8. The case 8 has, in one side surface, a peephole 10 through which a subject looks at the liquid-crystal display 1 installed in the case 8, and a jaw supporting base 9 for supporting a jaw of the subject is installed on the side surface.

The liquid-crystal display 1 (a display means) shows a fixed eye-target F for fixing a line of sight of the subject and a light stimulus eye-target L for giving a light stimulus to a pupil of the subject. A showing content of the liquid-crystal display 1 is controlled by the computer 6. As an example, the liquid-crystal display 1 has a 19-inch diagonal screen, and has a SXGA resolution (1280 by 1024 dots), and has maximal brightness of 400 cd/m$^2$, and has a contrast ratio of 450 to 1 (450:1), and has display colors of about 16.77 million, and has a view angle of 160 degrees in vertical and horizontal directions, and has a response speed of 12 ms. A distance between the liquid-crystal display 1 and the peephole 10 is about 29 cm, and therefore it is possible to measure a visual field within a range of ±26 degrees angle in the horizontal direction and ±21 degrees angle in the vertical direction. By using the liquid-crystal display 1 as a display means, it is possible to separately adjust the background luminance of the screen and the brightness of the light stimulus eye-target. Therefore, it is possible to easily generate pupillary light reflex by giving an intended brightness difference to the background luminance and the brightness of the light stimulus eye-target to give a sufficient light stimulus to a pupil P of the subject. Furthermore, because it is not necessary for the perimeter to darken the background luminance more than necessary, a time for the subject to adapt to darkness of the background (namely, a dark adaptation time) is short, so that a time for the inspection of the visual field can be reduced. Of course, because it is also possible to change the size, the shape, and the movement of the eye-target freely, it is possible to show an optimal eye-target according to the subject. The background luminance is preferably set to a range of about $3.18 \times 10^{-1}$ to 3.18 cd/m$^2$ (namely, 1 to 10 asb (where 1 asb=1/$\pi$ cd/m$^2$)). The brightness of the light stimulus eye-target is preferably set to a range of about 286 to 382 cd/m$^2$ (namely, 900 to 1200 asb).

The infrared light-emitting diodes 2 (an infrared light irradiating means) are installed at a diagonal upward position and an diagonal downward position with respect to an eye E of the subject S, respectively, so that they does not block the view of the subject. The infrared light-emitting diodes 2 irradiate infrared light with a wavelength of about 850 nm to the eye E of the subject.

The CCD camera 3 (an imaging means) has a 400,000 pixel resolution, and has sensitivity to the infrared light, so it can take an image of the eye E of the subject by using the infrared light of the infrared light-emitting diodes 2 under a dark environment where there is a little amount of light of natural light. Because the human retina does not perceive the infrared light, the pupillary light reflex is not caused by the infrared light of the infrared light-emitting diodes 2.

The half mirror 4 is a so-called hot mirror, and is formed by coating a surface of a glass plate with a filter having a property which reflects the infrared light with a wavelength of about 850±50 nm and transmits visible light with wavelengths of 450 to 650 nm. The half mirror 4 is disposed between the eye E of the subject and the liquid-crystal display 1, for example, in front of the eye E of the subject, so that a direction of the normal thereto tilts at about 45 degrees with respect to a light path. Because the light form the liquid-crystal display 1 passes through the half mirror 4 and enters the eye E of the subject, the subject can see the screen of the liquid-crystal display 1 through the half mirror 4. The light irradiated from the infrared light-emitting diodes 2 and reflected by the eye E of the subject is totally reflected by the half mirror 4, and enters the CCD camera 3 disposed above the half mirror 4.

The image processing device 5 (a pupil detection means) processes the image taken by the CCD camera 3, and measures a pupil diameter by extracting a part of the pupil from the image of the eye E, and it outputs the measuring result of the pupil diameter to the computer 6.

The computer 6 is connected to the image processing device 5 and the liquid-crystal display 1, and it has a function (an eye-target control means) of controlling the showing content of the liquid-crystal display 1 and showing the fixed eye-target and the light stimulus eye-target at a plurality of predetermined positions on the liquid-crystal display 1 and has a function (a visual field measuring means) of measuring the visual field based on the change of the pupil diameter of the subject detected by the image processing device 5 when the light stimulus eye-target is displayed in a condition where the subject looks at the fixed eye-target. These functions are realized by software (programs). The computer 6 is also connected to the operating switch 7, and it can receive an operation signal from the operating switch 7 according to an operation of the subject.

Black-body coating having emissivity of about 1.0 is applied to an inner surface of the case 8 and all parts inside the case 8 except for a viewing area of the liquid crystal-display 1, an emission surface of the infrared light-emitting diodes 2, an acceptance surface of the CCD camera 3, and a half mirror 4. The irradiated light from the liquid-crystal display 1 is absorbed by the black-body coating, so that a case where the light is reflected by other parts and enters unnecessary parts of the eye of the subject and an accurate perimetry can not be performed is prevented. As substitute for applying the black-body coating, an antireflection coating having low reflectance may be applied.

Figure 3:
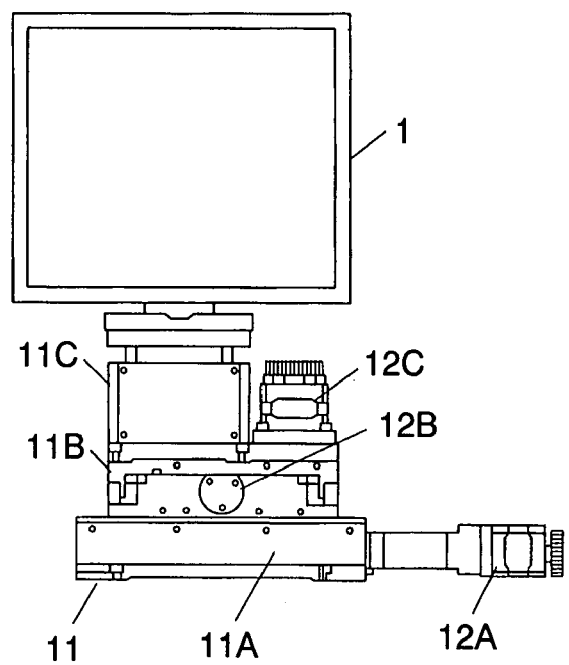
FIG. 3 is a view for explaining an installation method of a liquid-crystal display of the perimeter of FIG. 1.

As shown in FIG. 2 and FIG. 3, the liquid-crystal display 1 is mounted on a display position adjusting mechanism 11 (a display position adjusting means) which can adjust the position of the liquid-crystal display 1 in a vertical direction and/or a horizontal direction and/or a back-and-forth direction with respect to the peephole 10. The display position adjusting mechanism 11 comprises an X-axis table 11A, which is driven by a stepping motor 12A and is movable in the horizontal direction (an X-axis direction) with respect to the peephole 10, a Y-axis table 11B, which is installed on the X-axis table 11A and is driven by a stepping motor 12B and is movable to the back-and-forth direction (a Y-axis direction) with respect to the peephole 10, and a Z-axis table 11C, which is installed on the Y-axis table 11B and is driven by a stepping motor 12C and is movable in the vertical direction (a Z-axis direction) with respect to the peephole 10. The liquid-crystal display 1 is mounted on the Z-axis table 11C. It is possible to adjust the center of the liquid-crystal display 1 to the center of the right or left eye of the subject S in a condition where the subject S puts his jaw on the jaw supporting base 9, by adjusting the positions of the X-axis table 11A and the Z-axis table 11C, whereby it is possible to measure the visual field by using the liquid-crystal display 1 having a small screen. Furthermore, even if the subject S is myopia or hyperopia, it is possible to move the liquid-crystal display 1 to a position where the subject S can come into focus, by moving the Y-axis table 11B in the back-and-forth direction. Therefore, the subject S can perform the examination of the visual field without glasses or contact lenses, so that it is possible to measure the visual field more accurately.

Figure 4A:
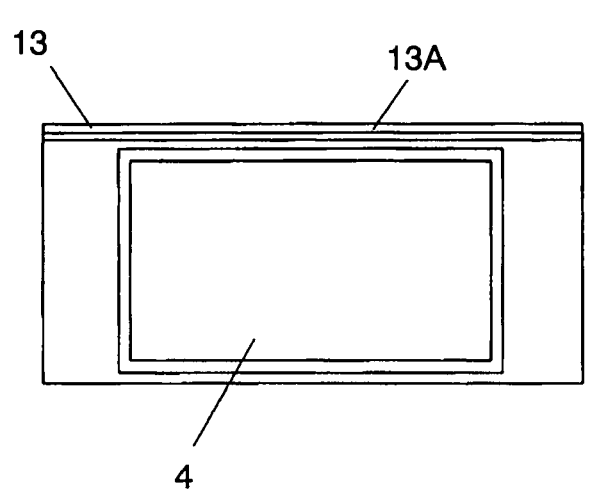
FIG. 4A is a view for explaining an installation method of a CCD camera of the perimeter of FIG. 1.
Figure 4B:
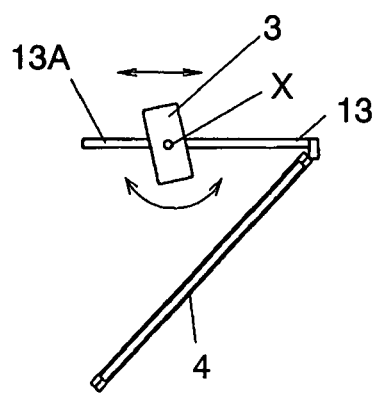
FIG. 4B is a view for explaining an installation method of a CCD camera of the perimeter of FIG. 1.

As shown in FIGS. 4A and 4B, the CCD camera 3 is attached to an attachment plate 13 disposed in a nearly horizontal position above the half mirror 4 so that the CCD camera 3 is movable in the back-and-forth direction and is rotatable about the X-axis. The imaging position and the imaging direction of the CCD camera 3 can be adjusted so that the center of the CCD camera 3 corresponds with the position of the pupil P of the subject, by moving the CCD camera 3 in the back-and-forth direction and by rotating the CCD camera 3 about the X-axis by using an imaging device adjusting means (not shown) such as a servomotor. Furthermore, it is possible to adjust the angle of the eye E reflected in the half mirror by rotating the CCD camera 3 about the X-axis. Therefore, it is possible to take an image of the pupil so that eyelashes do not overlap with the pupil P by adjusting the imaging angle of the CCD camera 3 to an angle where the CCD camera looks up at the eye from downside, whereby it is possible to prevent detection accuracy of the pupil diameter from being lowered by the eyelashes. Preferably, the computer 6 includes an imaging device control function (an imaging device control means) which controls the imaging device adjusting means, such as a servomotor, and adjusts the imaging position and the imaging direction of the CCD camera 3 so that the pupil diameter of the subject peaks (in other words, the pupil diameter of the subject reaches its maximum.). In this case, it is possible to automatically adjust the position and the imaging direction of the CCD camera 3 to an optimal position and optimal imaging direction.

Figure 5:
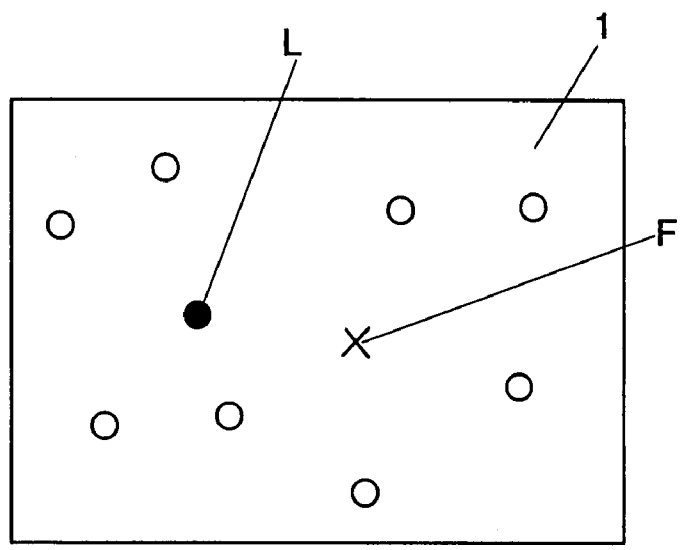
FIG. 5 is a view showing one example of a screen of the liquid-crystal display of the perimeter of FIG. 1.

Next, a measurement principle of the perimeter of the present invention will be described below. FIG. 5 shows a screen of the liquid-crystal display 1, and the fixed eye-target F is displayed at the center of the screen. The subject is instructed to gaze at the fixed eye-target F with one eye, and while the subject gazes at the fixed eye-target with one eye, the computer 6 shows the light stimulus eye-target L at a plurality of predetermined positions of the screen one after another randomly. In FIG. 5, a "●" mark shows one example of the light stimulus eye-target L currently displayed, and "○" marks show other examples of the showing position of the light stimulus eye-target L.

Figure 6A:
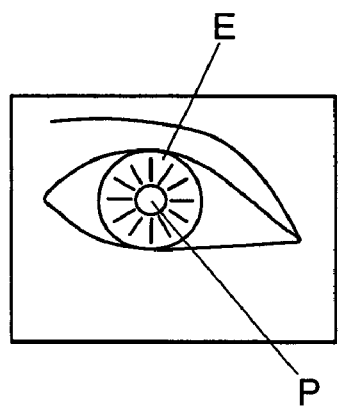
FIG. 6A is a view showing one example of an image taken by the CCD camera in the perimeter of FIG. 1.

The CCD camera 3 takes an image of the eye E at the time when the light stimulus eye-target L was shown using the infrared light of the infrared light-emitting diodes 2. FIG. 6A shows one example of the taken image.

Figure 6B:
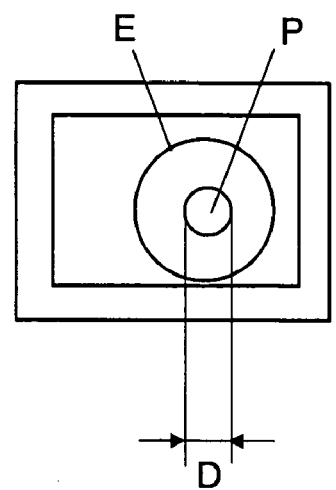
FIG. 6B is a view showing one example of a detected pupil diameter in the perimeter of FIG. 1.

As shown in FIG. 6B, the image processing device 5 extracts the pupil P from the taken image, and detects the pupil diameter D.

By the way, the size of the pupil is adjusted by a musculus sphincter pupillae and a musculus dilator pupillae, and the musculus sphincter pupillae is controlled by parasympathetic nerve system and the musculus dilator pupillae is controlled by sympathetic nervous system. Therefore, when a light stimulus is given to the eye E at an arbitrary position in a normal visual field area, this information is transmitted to the parasympathetic nerve system, and the musculus sphincter pupillae is reflexively contracted. When the light stimulus is removed after that, pupillary dilation occurs. This neurotransmission is a brain-stem reflex, so it is normally impossible for the subject to control it on a voluntary basis, and it occurs unconsciously with respect to the light stimulus. This is called a pupillary light reflex, and the stronger the light stimulus is, the larger the reaction of the pupillary light reflex becomes. In other words, it is deemed that a showing position of the light stimulus eye-target where a large reaction occurs has high retina sensitivity, and a showing position of the light stimulus eye-target where a small reaction occurs has low retina sensitivity.

Figure 7:
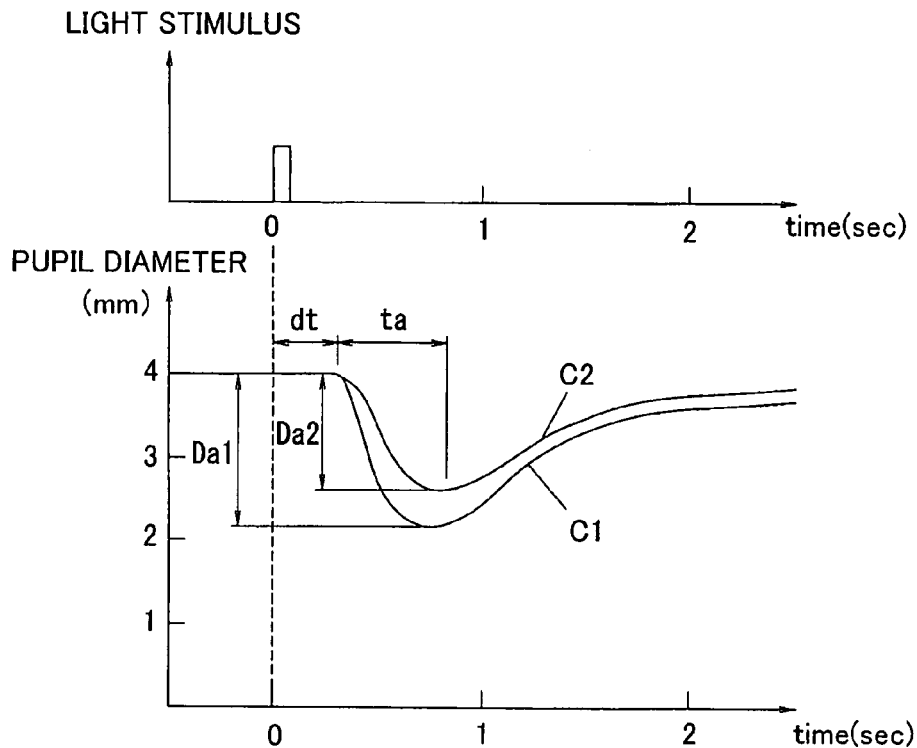
FIG. 7 is a view for explaining a measurement principle of the perimeter of FIG. 1.

FIG. 7 shows one example of the change of the pupil diameter caused by the pupillary light reflex. When the computer 6 shows the light stimulus eye-target at an arbitrary position for 0.1 second, miosis (constriction of the pupil) occurs after a delay time dt (latent time) of about 0.2 to 0.3 second. The diameter of the pupil reaches its maximum shortening point (a minimal value) after a lapse of time ta from the beginning of the miosis. The pupil diameter dilates gradually after it reached the minimal value (so-called pupillary dilation). In FIG. 7, curved lines C1 and C2 show changes of the pupil diameter at the time when the light stimulus eye-target were given to two different positions of the visual field area. As compared with the curved line C1, the curved line C2 has a small range of the change of the pupil diameter with respect to the light stimulus (that is, D1>D2.). When the change of the pupil diameter is small, like the curved line C2, it is deemed that an optic nerve located at the position where the light stimulus eye-target was shown has some abnormalities, whereby the sensitivity of the visual field is lowered.

The computer 6 (the visual field measuring means) calculates a maximum miosis amount, a miosis ratio (a ratio of constriction of a pupil, that is, a ratio of the maximum miosis amount to an initial size of a pupil), miotic velocity, and mydriatic velocity, based on the change of the pupil diameter detected by the image processing device 5.

Figure 8:
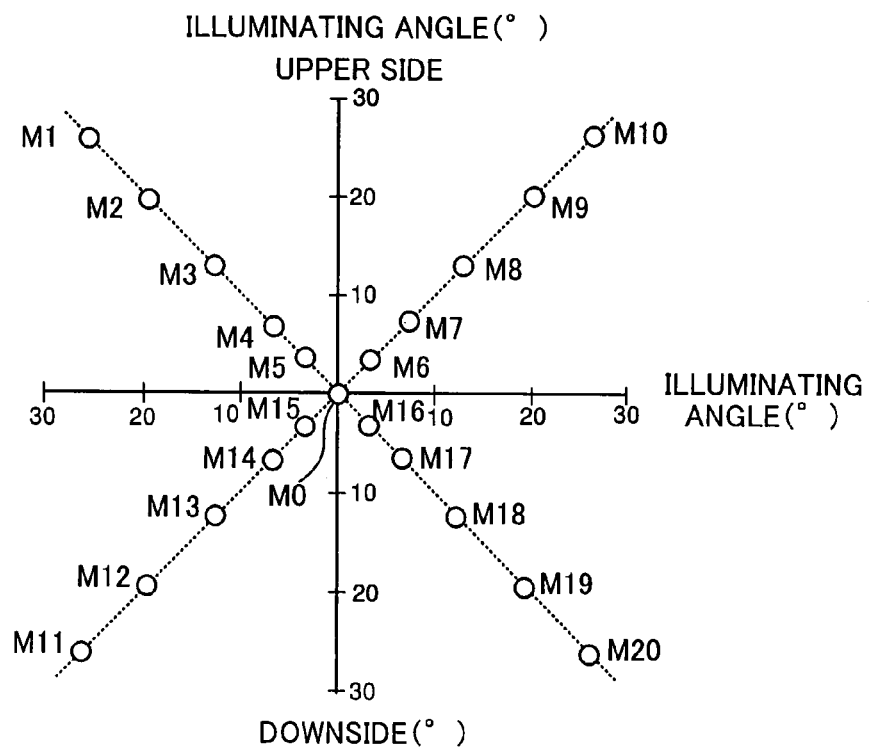
FIG. 8 is a view showing one example of a showing position of an eye-target in the perimeter of FIG. 1.

One example of an actual measuring result of the visual field of a subject of glaucoma measured by using the above principle will be explained below using FIGS. 8 to 11B. In this measurement, the fixed eye-target F was shown at the center of the screen, and the subject was instructed to gaze at the fixed eye-target F with one eye, and as shown in FIG. 8, the light stimulus eye-target L of a white pulse was shown randomly at a plurality of predetermined positions M0 to M20 on a line running diagonally left on the visual field of the subject, while the subject at gazed the fixed eye-target F, and the computer 6 calculated the miosis ratio from the pupil diameter D measured by the image processing device 5. The background luminance of the liquid-crystal display 1 was about 0.5 cd/m$^2$, the brightness of the light stimulus eye-target was about 300 cd/m$^2$, the size of the light stimulus eye-target was 2.0 deg, and the display time (showing time) of the light stimulus eye-target was about 0.2 second.

Figure 9A:
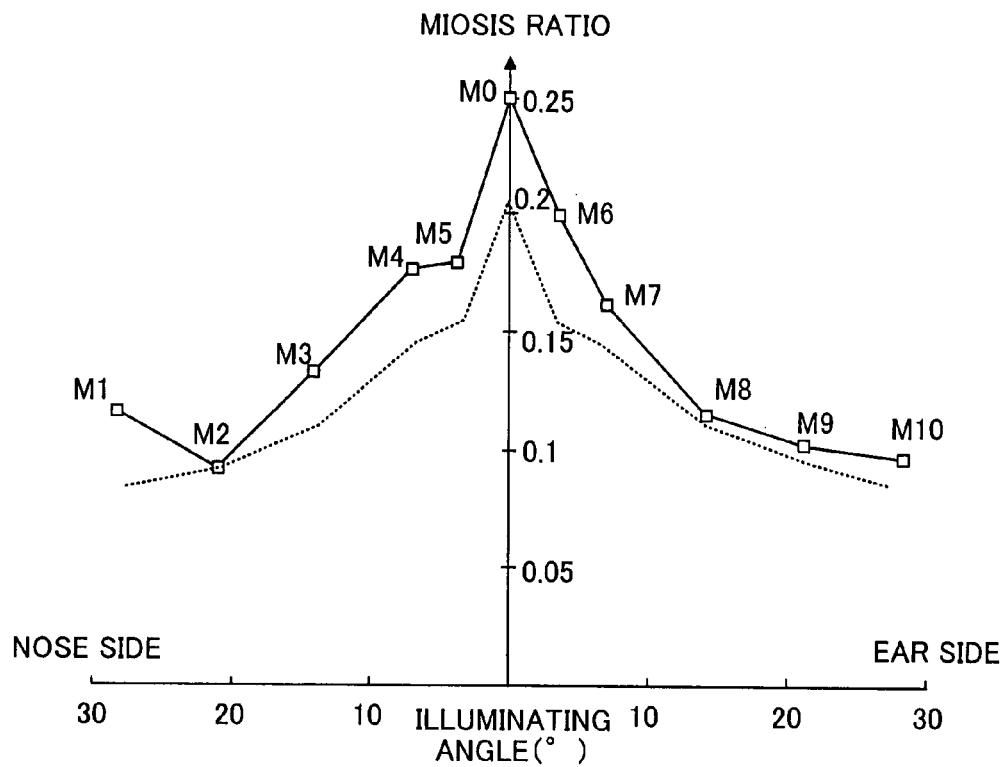
FIG. 9A is a view showing one example of a measured miosis ratio in the perimeter of FIG. 1.

FIG. 9A is a measuring result of the upper visual field of the right eye of the subject. That is, a relation between the miosis ratio at the time when the light-stimulus eye-target L was shown at each position M0 to M 10 of FIG. 8 and a showing position (an illuminating angle) of the light stimulus eye-target is shown in graphical form. A solid line indicates the measuring result, and a dashed line indicates the miosis ratio of a normal person. FIG. 9A indicates that the miosis ratio of the subject is greater than or equal to that of the normal person over all illuminating angles. Therefore, the upper visual field of the right eye of the subject is judged to be normal.

Figure 9B:
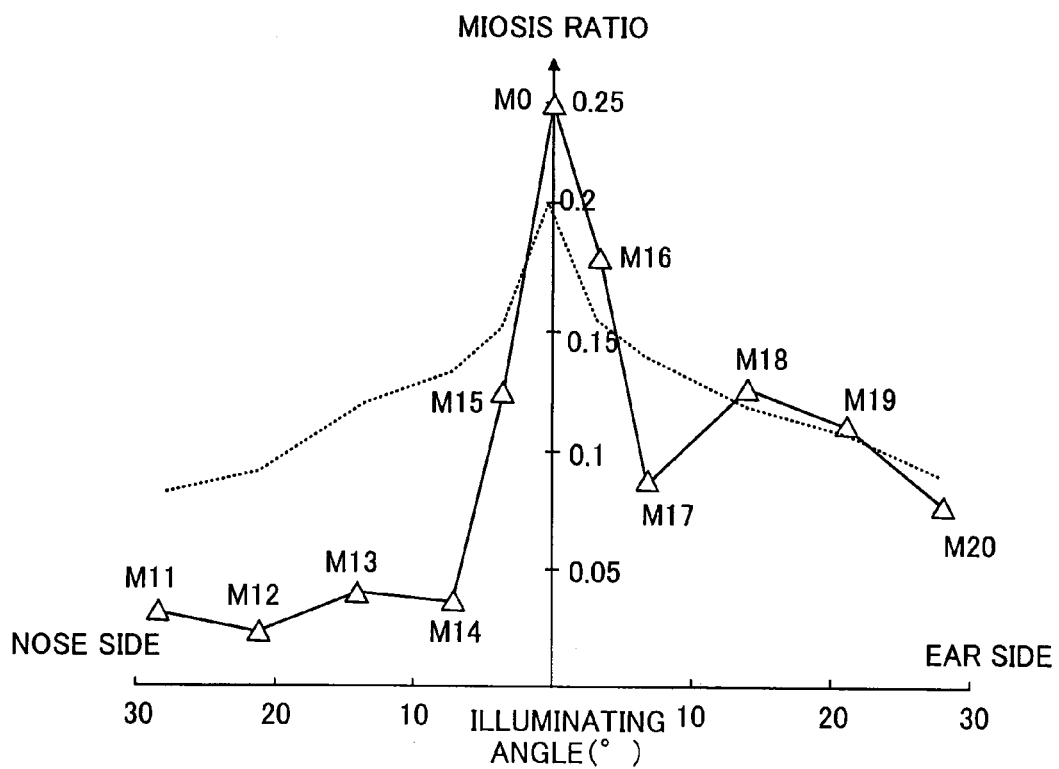
FIG. 9B is a view showing another example of a measured miosis ratio in the perimeter of FIG. 1.

On the other hand, FIG. 9B is a measuring result of the lower visual field of the right eye of the subject. That is, a relation between the miosis ratio at the time when the light-stimulus eye-target L was shown at each position M11 to M 20 of FIG. 8 and a showing position (an illuminating angle) of the light stimulus eye-target is shown in graphical form. As is the case with FIG. 9A, a solid line indicates the measuring result, and a dashed line indicates the miosis ratio of a normal person. FIG. 9B indicates that, in a nose side area of the subject (that is, the positions M11 to M15) and a part of an ear side area of the subject (that is, the positions M17 and M20), the miosis ratio of the subject is lower than that of the normal person. That is, it is deemed that the sensitivity of the visual field of the subject in these areas has deteriorated.

Figure 10:
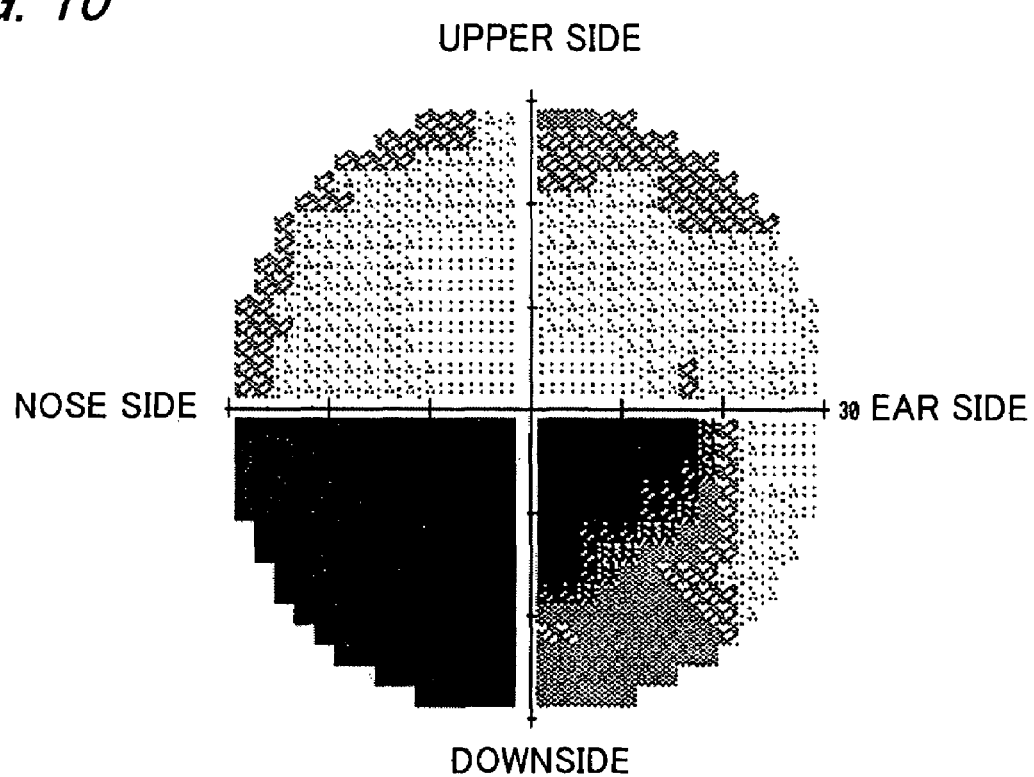
FIG. 10 is a view showing, in gray scale, a measurement result of a static perimetry performed to a subject of FIGS. 9A and 9B at the same time.

In addition, FIG. 10 is a measuring result of a static perimeter (a subjective perimeter) performed to the same subject at the same time. In this inspection using the static perimeter, the subject was instructed to push an operating switch when he or she looked at the light stimulus eye-target, and if the subject pushed the operating switch when the light stimulus eye-target was shown, the showing position was judged to be a normal visual field area of the subject, and if the subject did not push the operating switch when the light stimulus eye-target was shown, the showing position was judged to be an abnormal visual field area. And, the visual field of the subject was expressed by a gray scale in which the normal visual field area was expressed by a white color and the abnormal visual field area was expressed by a black color. FIG. 10 indicates that, as is the cases with the measuring result of FIGS. 9A and 9B, the upper area of the subject is a normal visual field area, and a part of the lower area of the subject is an abnormal visual field area.

In the perimeter of the present invention, it is also possible to perform the same inspection as the above inspection using the static perimeter by using the operating switch 7, and by performing the subjective perimetry in combination with the objective perimetry, it is possible to increase the reliability of the measuring result.

Figure 11A:
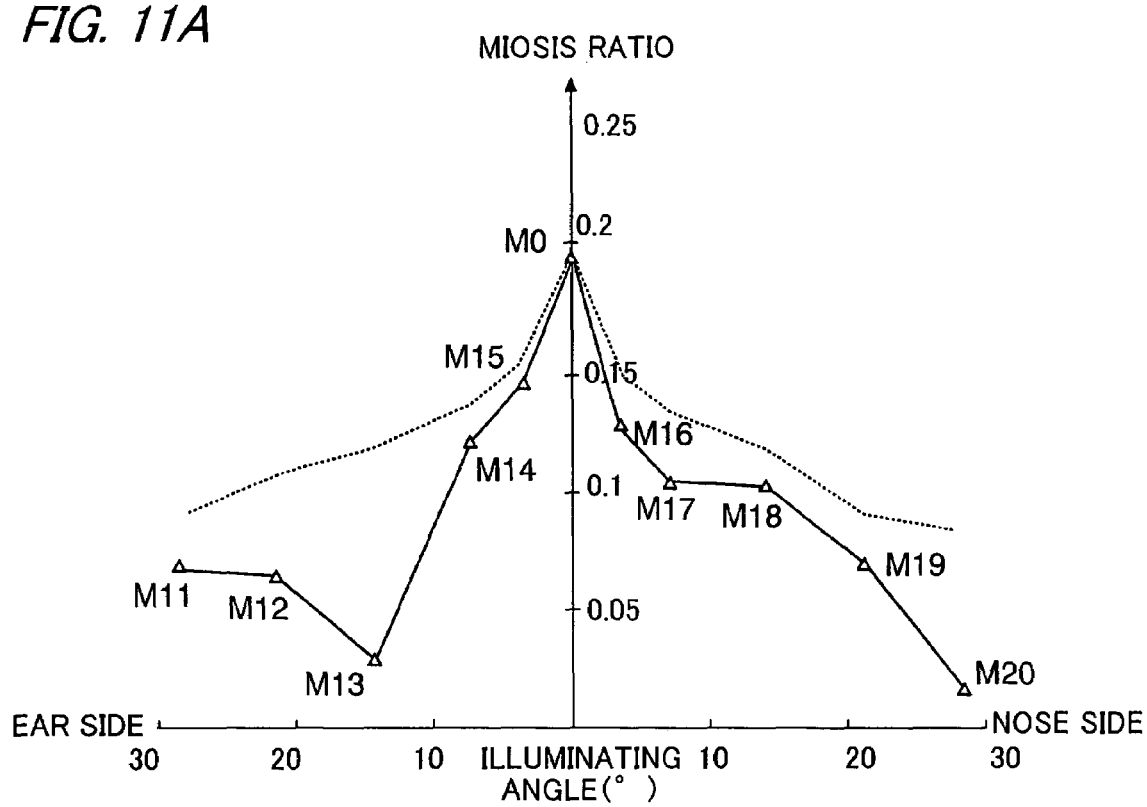
FIG. 11A is a view showing another example of the measured miosis ratio in the perimeter of FIG. 1.
Figure 11B:
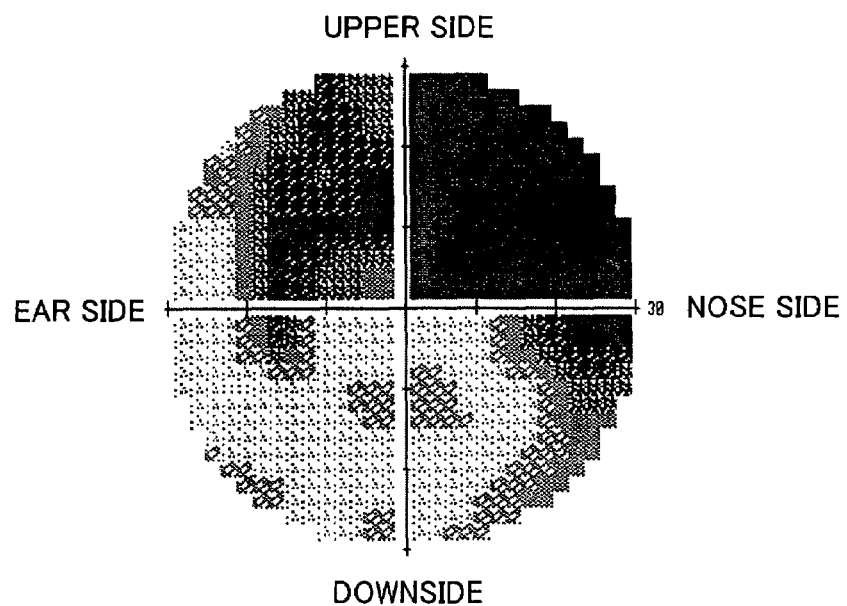
FIG. 11B is a view showing, in gray scale, a measurement result of a static perimetry performed to a subject of FIG. 11A at the same time.

By the way, FIG. 11A shows an objective measuring result of the lower visual field of the left eye of the subject in using the perimeter of the present invention, and FIG. 11B is a subjective measuring result of the visual field of the left eye of the subject in using a static perimeter. Seeing FIG. 11A, the miosis ratio declines in the area on the ear side of the subject (around the position M13), so it is deemed that the sensitivity of the visual field of the subject has deteriorated. However, seeing FIG. 11B, the lower area of the ear side of the subject is white, that is, the area is judged to be a normal visual field area. In other words, although the area was judged to be a normal visual field area in the subjective result, the area was judged that the sensitivity of the visual field had deteriorated in the objective result. This is deemed that the objective inspection seizes a symptom in an early stage before a subjective symptom appears on the subject. As above, the objective perimeter is expected to seize a symptom in an early stage and to halt the progression of the symptom.

Although, in the above measurement examples, the computer 6 calculates the miosis ratio from the change of the pupil diameter as an indicator for measuring the visual field of the subject, the computer 6 (the visual field measuring means) may have a function of judging whether a position where the light stimulus eye-target was shown is a normal visual field area of the subject, in addition to the function of calculating the miosis ratio. For example, the computer 6 compares the miosis ratio and a predetermined threshold, and if the miosis ratio is greater than the threshold, the computer judges that it is a normal visual field area, and if the miosis ratio is smaller, the computer judges that it is an abnormal visual field area. In this case, it is preferable that the threshold is varied according to age and/or sex of the subject. Or, the visual field of the subject may be divided into a plurality of areas (for example, four areas composed of a first quadrant (an upper right quadrant) to a fourth quadrant (a lower right quadrant)), and the divided area where a density of deteriorated sensitivity of visual field is high may be judged as the abnormal visual field area.

The computer 6 (the eye-target control means) may have a function of changing a color of the light stimulus eye-target. In this case, because the sensitivity of a retina varies according to a color wavelength, it becomes possible to inspect a particular retina area by changing the color of the light stimulus eye-target. That is, generally, retina cells can be classified into rod cells, which react to black and white, and cone cells, which react to a color, so, by showing colored light stimulus eye-target, it becomes possible to inspect the reaction of the cone series.

Although, in the above inspection, the light stimulus eye-target was shown only on the line running diagonally left on the visual field of the subject, the showing positions of the light stimulus eye-target are not limited to the above example.

Figure 12A:
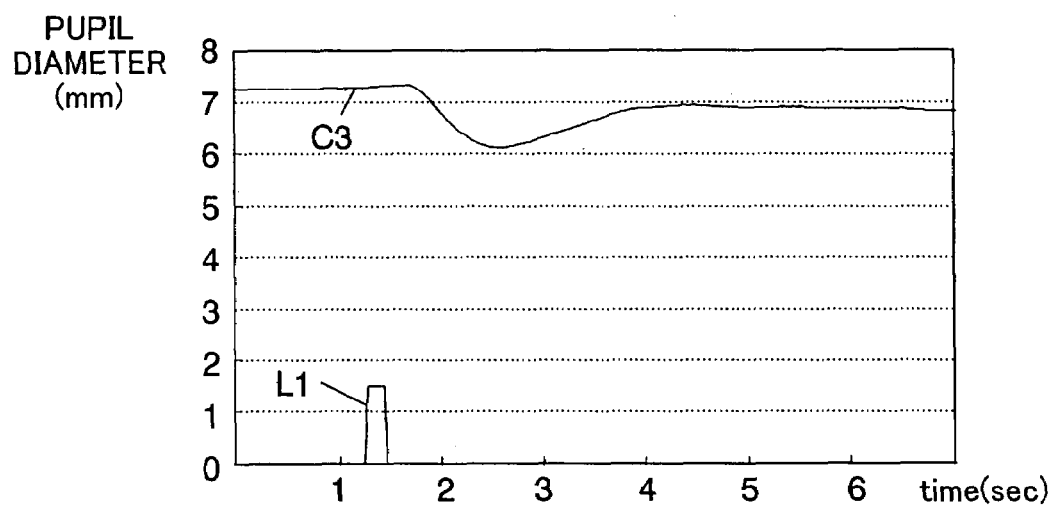
FIG. 12A is a view showing one example of the light stimulus eye-target in the perimeter of FIG. 1.
Figure 12B:
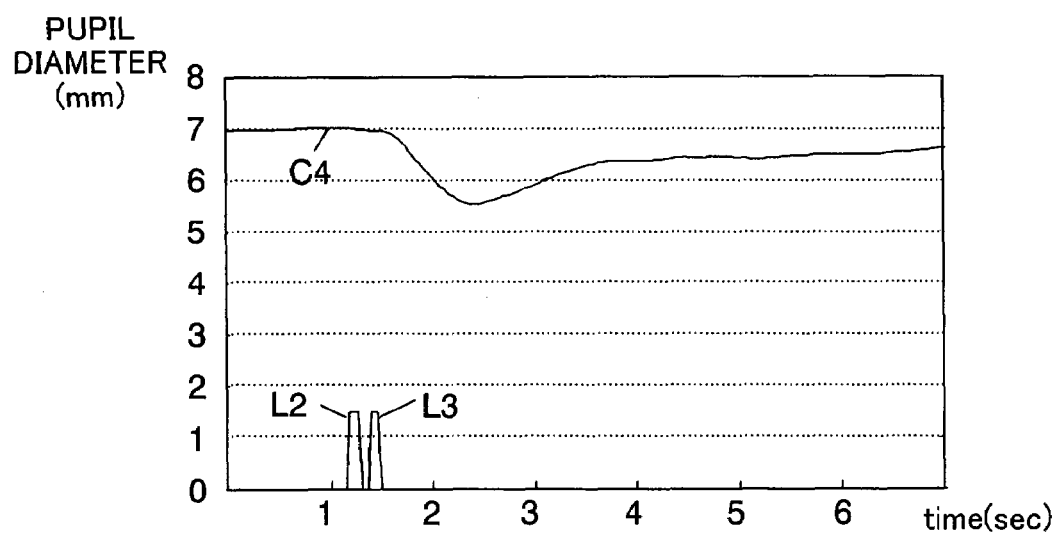
FIG. 12B is a view showing another example of the light stimulus eye-target in the perimeter of FIG. 1.

By the way, the miosis ratio tends to decrease with advancing age, so in some subjects, the pupillary light reflex may be small even when a pulse-like light stimulus is given. In such a case, it is preferable that a pulse-like light stimulus eye-target is shown at least twice in a row during the latent time. FIG. 12A shows a change of the pupil diameter (see a curved line C3) at the time when a pulse-like light stimulus L1 of 0.2 second was shown, and FIG. 12B shows a change of the pupil diameter (see a curved line C4) at the time when a pulse-like light stimulus of 0.1 second (see L2 and L3) was shown twice in a row at 0.1 second intervals. When comparing FIG. 12A with FIG. 12B, a total time of the light stimulus in each FIG. is 0.2 second, and they are equal to each other, but, the change of the pupil diameter of FIG. 12B is larger than that of FIG. 12A. As above, by showing the pulse-like light stimulus at least twice in a row, it is expected that large pupillary light reflex can be obtained.

Figure 13:
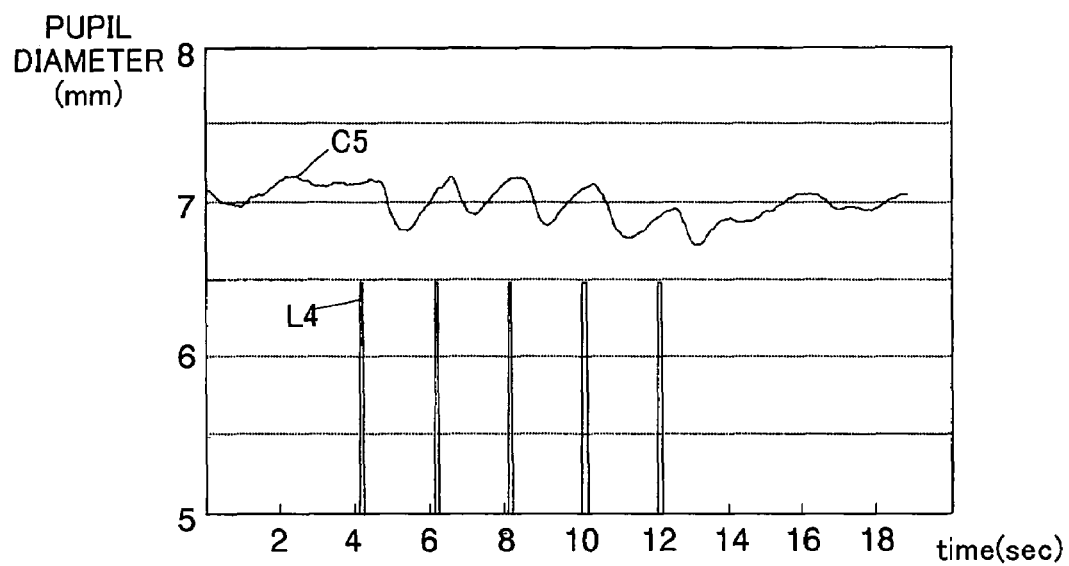
FIG. 13 is a view showing another example of the light stimulus eye-target in the perimeter of FIG. 1.

In addition, the size of the pupil diameter may wander even in a steady state where there is no light stimulus, and therefore there is a case where it is difficult to judge whether the change of the pupil diameter was caused by the light stimulus or not. In such a case, it is preferable that the light stimulus eye-target which changes periodically in intensity of light is shown on the liquid-crystal display. FIG. 13 shows one example of the change of the pupil diameter at the time when an optical pulse train L4, in which a pulse was shown five times in a row at 2-second intervals, was shown at the center of the visual field, as the light stimulus eye-target which changes periodically in intensity of light. In FIG. 13, although the pupil diameter wanders even before the light stimulus eye-target was shown, when the pulse train L4 of five pulses was shown, the change of the pupil diameter also occurs five times in synchronization with the pulse train L4 (see, a curved line C5). As above, when the intensity of light is changed periodically, the triggered change of the pupil diameter gets periodicity if the visual field of the subject is normal. Therefore, when the change of the pupil diameter accompanied with periodicity as FIG. 13 is observed, it is highly possible that the change was triggered by the light stimulus. Although FIG. 13 shows one example of a case where the light stimulus eye-target which changes periodically in intensity of light was shown at the center of the visual field, the same holds for a case where the light stimulus eye-target which changes periodically in intensity of light is shown at various areas of the visual field. Therefore, it is possible to measure the visual field of the subject by showing the light stimulus eye-target which changes periodically in intensity of light at a plurality of predetermined positions of the liquid-crystal display and measuring the change of the pupil diameter at the time.

Judgment of synchronism between the period of the intensity of light of the light stimulus eye-target and the period of the change of the pupil diameter can be made by checking whether the number of the change of the light stimulus P corresponds to the number of the change of the pupil diameter (in other words, the number of the repetition of a local minimal value and a local maximal value) or not. Or, the synchronism may be judged by applying an autocorrelation analysis to a data string of the pupil diameter and by checking its periodicity.

It is also preferable that the computer 6 (the visual field measuring means) has a function of calculating the synchronism between the period of the intensity of light of the light stimulus eye-target and the period of the change of the pupil diameter by using e.g. the autocorrelation analysis and notifying the calculated synchronism to a measurer (that is, a doctor and so on). In this case, the measurer can judge the reliability of the measurement result by checking the synchronism between the period of the intensity of light of the light stimulus eye-target and the period of the change of the pupil diameter.

In a case where the pupil diameter changes periodically, it is possible to easily obtain a local minimal value and a local maximal value of the pupil diameter. Therefore, it is preferable that the computer 6 (the visual field measuring means) defines the difference between the local minimal value and the local maximal value of the pupil diameter, namely an oscillation range of the pupil diameter, as the magnitude of the change of the pupil diameter. Or, amplitude of the pupil diameter, which is half of the oscillation range, may be defined as the magnitude of the change of the pupil diameter. As shown in FIG. 13, when a plurality of differences between the local minimal value and the local maximal value can be obtained, an average value thereof may be defined as the magnitude of the change of the pupil diameter of the showing position of the light stimulus eye-target. In this case, it is possible to moderate fluctuations (unevenness) of the pupil diameter.

It is preferable that the computer 6 (the visual field measuring means) calculates a ratio between the magnitude of the change of the pupil diameter, which was obtained as above, and the intensity of light of the light stimulus eye-target, and measures the sensitivity of the visual field of the subject based on the ratio. In a case where a very minute retina area is abnormal but the periphery thereof is normal, if the irradiating range of the light stimulus eye-target to the retina is astride the abnormal area and the normal area, a pupillary reaction may occur. In such a case, it is deemed that the magnitude of the pupillary reaction varies according to the ratio between the magnitude of the abnormal area and the magnitude of the normal area, so it is possible to calculate the sensitivity of the visual field by measuring the magnitude of the pupillary reaction. The magnitude of the pupillary reaction depends on the intensity of the light stimulus, and the stronger the light stimulus is, the greater the pupillary reaction becomes. Therefore, the computer 6 can measure the sensitivity of the visual field of the subject by calculating the ratio between the magnitude of the change of the pupil diameter and the intensity of light of the light stimulus eye-target (that is, the magnitude of the pupillary reaction/the magnitude of the light stimulus eye-target). When the ratio is small, that means that the pupillary reaction to the strong light is small, so it is deemed that the sensitivity of the retina has deteriorated.

Figure 14:
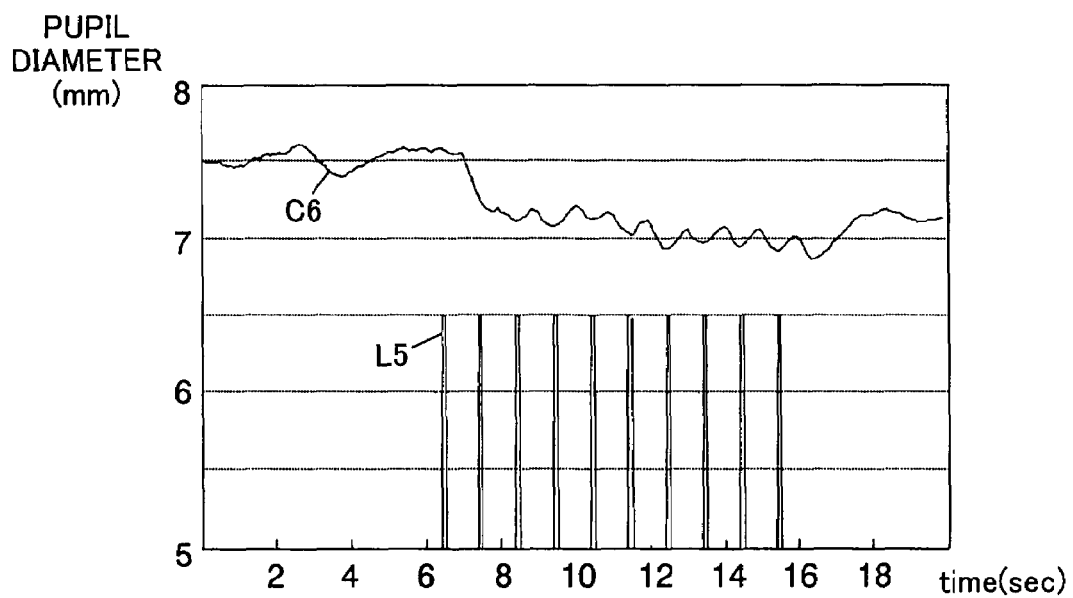
FIG. 14 is a view showing another example of the light stimulus eye-target in the perimeter of FIG. 1.

In a case where the light stimulus eye-target which changes periodically in intensity of light is shown, it is preferable that the computer 6 (the eye-target control means) has a function of changing the period of the intensity of light. FIG. 14 shows an example of a case in which an optical pulse train L5 in which a pulse was shown at one second intervals was shown. When comparing the FIG. 14 in which a pulse was shown at one second intervals with the FIG. 13 in which a pulse was shown at 2-second intervals, the magnitude of the pupil diameter of FIG. 14 is smaller than that of FIG. 13, and the feature of the periodicity of FIG. 14 is unclear. The earlier the next light stimulus is shown before a pupil dilates sufficiently, the shorter the period become, and the change of the magnitude of the pupillary reaction becomes small. Therefore, in order to increase readability of the magnitude of the change of the pupil diameter, it is preferable that the period is not too short. On the other hand, if the period is long, the inspection time also becomes long, whereby a burden on the subject becomes large. So, it is preferable that the computer 6 has the function of changing the period of the intensity of light, and when the periodicity of the change of the pupil diameter is clear, it shortens the period of the intensity of light so that the inspection time is reduced, and when the periodicity of the change of the pupil diameter is unclear, it lengthens the period of the light stimulus presentation so that the visibility of the waveform is increased.

Although the intensity of light is changed in a constant period in FIGS. 13 and 14, it is not necessary that the intensity of light changes in a strict constant period. It is possible to enlarge the change of the pupil diameter by measuring the change of the pupil diameter D in real time and by varying the period of the intensity of light according to the period of the pupillary reaction and by showing the light stimulus eye-target on cue.

Figure 15:
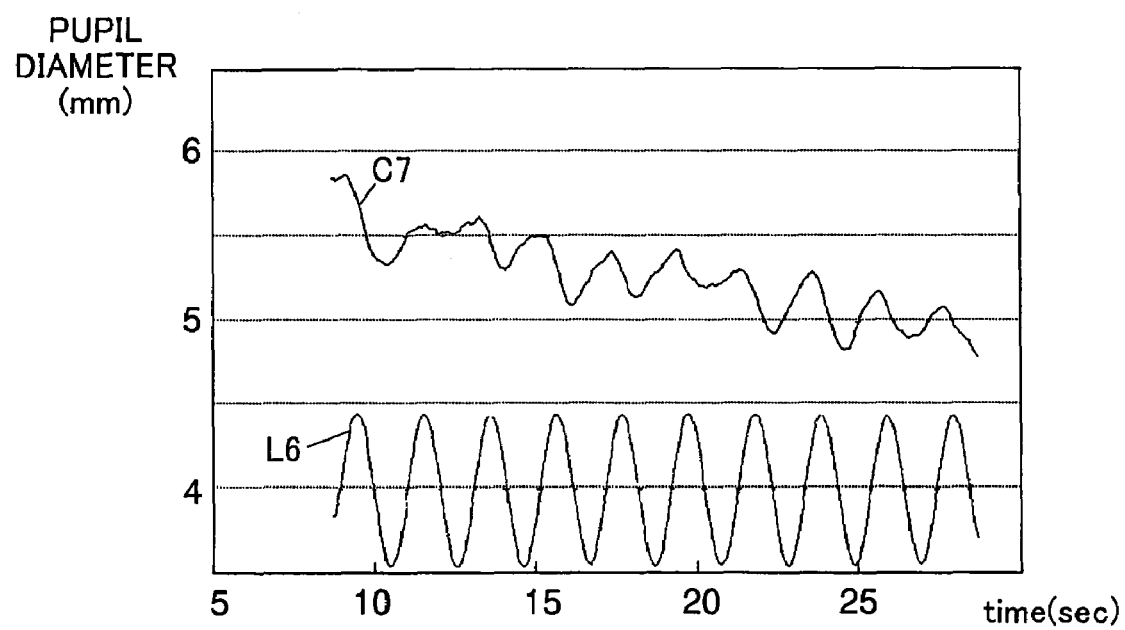
FIG. 15 is a view showing another example of the light stimulus eye-target in the perimeter of FIG. 1.

Although, in FIG. 13, the optical pulse train L4 is shown as the light stimulus eye-target which changes periodically in intensity of light, the eye-target L6 which changes in a sine wave manner in intensity of light may be used as a substitute for the optical pulse train, as shown in FIG. 15. Seeing FIG. 15, when the eye-target L6 which changes in a sine wave manner in intensity of light is shown, although the change of the pupil diameter (see a curved line C7) is a little off from the sine wave, the change of the pupil diameter also changes in response to the light stimulus. When the change of the pupil diameter accompanied with periodicity as FIG. 15 is observed, it is deemed that it is highly possible that the change was triggered by the light stimulus. As above, when the eye-target L6 which changes in a sine wave manner in intensity of light is used as a substitute for the optical pulse train, it is possible to easily judge whether the change of the pupil diameter is caused by the light stimulus or not.

In addition, in FIG. 15, an offset component (a DC value) of the pupil diameter is on a declining trend. When the change of the pupil diameter has such a trend, if a single light stimulus was used, it was very unclear whether the change of the pupil diameter was caused by a trend or caused by the light stimulus. However, because the pupil diameter changes periodically in FIG. 15, it is easily judged that the change is caused by the light stimulus and the corresponding retina area is normal.

Furthermore, it is also preferable that the computer 6 (the eye-target control means) has a function of changing a size of the light stimulus eye-target. In general, the larger the light stimulus eye-target is, the larger the magnitude of the pupillary light reflex becomes, and the readability of the waveform is increased. However, if the eye-target is large, the stimulation area to the retina is also large, so it is impossible to perform an accurate measurement. On the other hand, if the view angle of the eye-target is small, the readability of the waveform is decreased, but it is possible to perform an accurate measurement, and an early diagnostics of glaucoma and so on can be expected. That is, the readability of the waveform and the accurate measurement have a tradeoff relation. So, it is preferable that the computer 6 has a function of changing the size of the light stimulus eye-target, and it makes the eye-target small in a view direction in which an accurate measurement is desired, and it makes the eye-target large when it is desired that the readability of data is increased. In order to increase the readability of the waveform, when the eye-target is made small, it is preferable that the repeat count of the light stimulus eye-target is increased or the background luminance is reduced to make the change of the pupil large.

It should be noted that because the perimeter of this embodiment employs the liquid-crystal display 1 as the display means, it is possible to easily change the intensity, the period, and the size of the light stimulus eye-target as mentioned above.

Although this embodiment employs the liquid-crystal display 1 as the display device, a display device such as a CRT, a PDP, a ELD, a FED, and so on may be used as a substitute for the liquid-crystal display 1.

Furthermore, it is possible to constitute a head-mounted perimeter which has a small liquid-crystal display inside a goggles-shaped case.

As mentioned above, as many apparently widely different embodiments of this invention may be made without departing from the spirit and scope thereof, it is to be understood that the invention is not limited to the specific embodiments thereof except as defined in the appended claims.

The invention claimed is:

1. A perimeter comprising:
    a display means;
    an eye-target control means which shows a fixed eye-target for fixing a line of sight of a subject and a light stimulus eye-target for giving a light stimulus to a pupil of the subject at a plurality of predetermined positions on said display means;
    an infrared light irradiating means for irradiating infrared light to an eye of the subject;
    an imaging means for taking an image of the eye of the subject using the infrared light irradiated from said infrared light irradiating means;
    a case for housing said display means, said infrared light irradiating means, and said imaging means therein, said case having a peephole through which the subject looks at said fixed eye-target and said light stimulus eye-target displayed on said display means from outside;
    a pupil detection means for detecting a pupil diameter of the subject based on the image taken by said imaging means;
    a visual field measuring means for measuring a visual field of the subject based on a change of the pupil diameter of the subject detected by said pupil detection means when said eye-target control means shows the light stimulus eye-target in a condition where the subject looks at the fixed eye-target,
    wherein
    said display means comprises a display device capable of adjusting background luminance of a screen and brightness of the light stimulus eye-target separately.

2. The perimeter as set forth in claim 1, further comprising:
    a display position adjusting means capable of adjusting a position of said display means in a vertical direction and/or a horizontal direction and/or a back-and-forth direction with respect to said peephole.

3. The perimeter as set forth in claim 1, further including:
    an imaging device adjusting means capable of adjusting an imaging position and imaging direction of said imaging means.

4. The perimeter as set forth in claim 3, further comprising:
    an imaging device control means for adjusting the imaging position and the imaging direction of said imaging means through said imaging device adjusting means based on a detection result of said pupil detection means so that the pupil diameter of the subject peaks.

5. The perimeter as set forth in claim 1, further comprising:
    an operating switch which outputs an operation signal to said visual field measuring means in response to an operation of the subject,
    said visual field measuring means measuring the visual field based on the change of the pupil diameter of the subject and an input of the operation signal from the operating switch.

6. The perimeter as set forth in claim 1, wherein emissivity of an inner surface of said case is generally one.

7. The perimeter as set forth in claim 1, wherein said eye-target control means shows a pulse-like light stimulus eye-target at least twice in a row on said display means.

8. The perimeter as set forth in claim 1, wherein said eye-target control means shows the light stimulus eye-target which changes periodically in intensity of light on said display means.

9. The perimeter as set forth in claim 8, wherein said light stimulus eye-target is an optical pulse train.

10. The perimeter as set forth in claim 8, wherein the intensity of light of said light stimulus eye-target changes in a sine wave manner.

11. The perimeter as set forth in claim 8, wherein said eye-target control means has a function of changing a period of the intensity of light of the light stimulus eye-target.

12. The perimeter as set forth in claim 8, wherein said eye-target control means has a function of changing a size of the light stimulus eye-target.

13. The perimeter as set forth in claim 8, wherein said visual field measuring means has a function of calculating a magnitude of a change of the pupil diameter from an oscillation range of the pupil diameter or amplitude of the pupil diameter.

14. The perimeter as set forth in claim 13, wherein said visual field measuring means has a function of calculating a ratio between the magnitude of the change of the pupil diameter and the intensity of light of the light stimulus eye-target and measuring sensitivity of the visual field of the subject based on the ratio.

15. The perimeter as set forth in claim 8, wherein said visual field measuring means has a function of calculating synchronism between a period of the intensity of light of the light stimulus eye-target and a period of a change of the pupil diameter of the subject.

16. The perimeter as set forth in claim 1, wherein said visual field measuring means has a function of judging whether a position where the light stimulus eye-target was shown is a normal visual field area of the subject or not, based on a change of the pupil diameter of the subject.

17. The perimeter as set forth in claim 1, wherein said eye-target control means has a function of changing a color of the light stimulus eye-target.

* * * * *